United States Patent [19]

Fikentscher et al.

[11] Patent Number: 5,077,427
[45] Date of Patent: Dec. 31, 1991

[54] PREPARATION OF ALPHA-FORMYLAMINO NITRILES

[75] Inventors: Rolf Fikentscher, Ludwigshafen; Michael Kroener, Mannheim, both of Fed. Rep. of Germany

[73] Assignee: BASF Aktiengesellschaft, Ludwigshafen, Fed. Rep. of Germany

[21] Appl. No.: 627,021

[22] Filed: Dec. 13, 1990

[30] Foreign Application Priority Data

Dec. 22, 1989 [DE] Fed. Rep. of Germany ....... 3942575

[51] Int. Cl.$^5$ ............................................ C07C 255/00
[52] U.S. Cl. ..................................... 558/459; 546/330; 548/343; 548/505; 548/550; 548/561; 549/13; 549/76; 549/378; 549/426; 549/493; 558/404; 558/430; 558/434; 558/447; 558/448; 558/449
[58] Field of Search .............. 558/404, 430, 434, 447, 558/448, 449, 459; 546/330; 548/343, 505, 550, 561; 549/13, 76, 378, 426, 493

[56] References Cited

U.S. PATENT DOCUMENTS

| 2,720,540 | 10/1955 | Caverly | 558/459 |
| 3,174,992 | 3/1965 | McCracken | 558/459 |
| 3,822,306 | 7/1974 | Becke et al. | |

FOREIGN PATENT DOCUMENTS

| 598055 | 5/1960 | Canada | 558/459 |
| 1950280 | 4/1971 | Fed. Rep. of Germany | |
| 49-14423 | 2/1974 | Japan | 558/459 |

OTHER PUBLICATIONS

Aida et al., Chemical Abstracts, vol. 86, No. 43745q (1977), 89817t (1977).

Takagi et al., Chemical Abstracts, vol. 94, No. 121438y (1981).

Primary Examiner—Bruce Gray
Attorney, Agent, or Firm—John H. Shurtleff

[57] ABSTRACT

A process for preparing α-formylamino nitriles of the formula I

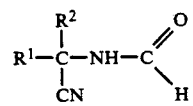

where $R^1$ and $R^2$ are each hydrogen or unsubstituted or substituted, with substituents which are inert under the reaction conditions, aliphatic or heteroaliphatic radicals with 1 to 10, cycloaliphatic or heterocycloaliphatic radicals with 3 to 6, aralphatic radicals with 7 to 12, heteroaralphatic radicals with 4 to 12, aromatic radicals with 6 to 10 or heteroaromatic radicals with 3 to 10 carbon atoms, by reacting cyanohydrins of the formula II

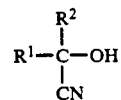

with the formamide III

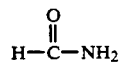

in the presence of acids, entails adding at least one ammonium salt to the reaction mixture.

8 Claims, No Drawings

PREPARATION OF ALPHA-FORMYLAMINO NITRILES

The present invention relates to a process for preparing α-formylamino nitriles of the formula I

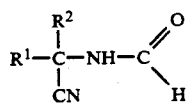

where $R^1$ and $R^2$ are each hydrogen or unsubstituted or substituted, with substituents which are inert under the reaction conditions, aliphatic or heteroaliphatic radicals with 1 to 10, cycloaliphatic or heterocycloaliphatic radicals with 3 to 6, araliphatic radicals with 7 to 12, heteroaraliphatic radicals with 4 to 12, aromatic radicals with 6 to 10 or heteroaromatic radicals with 3 to 10 carbon atoms, by reacting cyanohydrins of the formula II

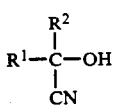

with formamide III

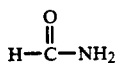

in the presence of acids.

U.S. Pat. No. 3,822,306 discloses that α-formylamino nitriles of the formula I with $R^1$ and/or $R^2$ not hydrogen can be obtained by the acid-catalyzed reaction of the corresponding cyanohydrins II with formamide III at from 60° to 180° C. A formamide excess of from 2 to 3 mole per mole of cyanohydrin II is preferably used for this. Although the process of DE-A 19 50 280 gives good results in the preparation of α-formylamino nitriles, for example the nitrile of N-formylalanine IV

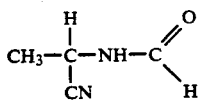

can be obtained in a yield of 82% in this way, starting from acetaldehyde cyanohydrin, the process did appear to be capable of improvement in some respects. Thus, for example, the preparation of the nitrile of N-formylalanine by this process gave rise, owing to a number of unknown side reactions, to 4 to 6 l of gas per liter of reaction liquid, the gas being essentially composed of a mixture of carbon monoxide and carbon dioxide plus about 5% of hydrogen cyanide, which meant that elaborate safety measures were needed for its disposal. This evolution of gas and the associated bumping makes it difficult to carry out the reaction safely, for which reason the reactor must be equipped with additional safety devices.

As a consequence of the said side reactions, the yield of formylamino nitrile in this process is only 75% of theory based on formamide III. In addition, under the reaction conditions the cyano groups of I and II were partially hydrolyzed by the water of reaction to the carboxamide, which likewise results in losses of yield.

It is an object of the present invention to find measures which make it possible to eliminate the disadvantages of this process and to improve its economics and the yield thereof.

We have found that this object is achieved by a process for preparing α-formylamino nitriles of the formula I

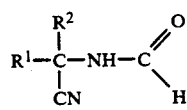

where $R^1$ and $R^2$ are each hydrogen or unsubstituted or substituted, with substituents which are inert under the reaction conditions, aliphatic or heteroaliphatic radicals with 1 to 10, cycloaliphatic or heterocycloaliphatic radicals with 3 to 6, araliphatic radicals with 7 to 12, heteroaraliphatic radicals with 4 to 12, aromatic radicals with 6 to 10 or heteroaromatic radicals with 3 to 10 carbon atoms, by reacting cyanohydrins of the formula II

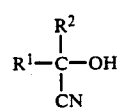

with formamide III

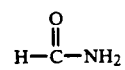

in the presence of acids, which comprises adding at least one ammonium salt to the reaction mixture.

Thus, the process according to the invention entails reacting cyanohydrins II with formamide III in accordance with equation (1)

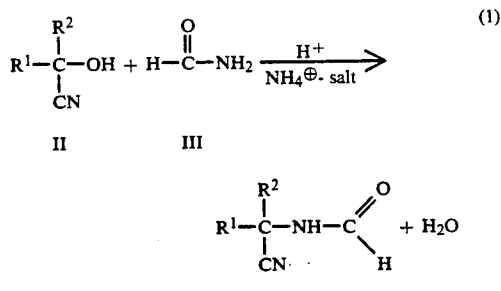

with acid catalysis and addition of one or more ammonium salts acting as cocatalysts to give the corresponding α-formylamino nitriles I.

The ammonium salts which can be used according to the invention are, in principle, those with any suitable anions such as formate, acetate, propionate, halide, hydrogen sulfate, dihydrogen phosphate, methanesulfonate, toluenesulfonate, lactate, oxalate, adipate, citrate etc. The ammonium salts preferably used in the process according to the invention are those of the acids used to catalyze the reaction according to the invention. Among these, the ammonium salts of lower carboxylic acids, especially $C_1$–$C_6$-monocarboxylic acids, are preferred. It is particularly advantageous to use ammonium formate. The ammonium salts, especially ammonium formate, are expediently added to the reaction mixture in amounts of from 0.05 to 0.5 mole, preferably from 0.1 to 0.3 mole, per mole of cyanohydrin II. It is possible to add larger amounts of ammonium salt. Of course, mixtures of different ammonium salts can also be added to the reaction mixture, but addition of one ammonium salt is generally preferred. The reaction according to the invention can be catalyzed by both mineral acids and organic carboxylic and/or sulfonic acids. Preferably used are lower aliphatic mono-, di- or tricarboxylic acids, especially $C_1$–$C_6$-monocarboxylic acids and particularly advantageously formic acid. The use of substituted carboxylic acids, for example hydroxy carboxylic acids or halo carboxylic acids, such as chloroacetic acid and trifluoroacetic acid, is likewise possible. The acids are usually employed in amounts of from 0.001 to 1, preferably from 0.1 to 0.3, mole of acid per mole of cyanohydrin. It is, of course, also possible to use mixtures of various acids but, for practical reasons, to simplify working up of the reaction mixture, it is preferable to use only one acid species as catalyst.

The process according to the invention can be carried out with equimolar amounts of cyanohydrin II and formamide III, but preferably excess formamide is used. As a rule, from 1.1 to 2.0, preferably 1.2 to 1.8, mole of formamide are employed per mole of cyanohydrin II, but larger excesses are also possible.

The reaction according to the invention is generally carried out at from 20° to 150° C., preferably from 60° to 120° C. and particularly advantageously at from 80° to 100° C. Above 120° C. the reaction is complete within a few minutes, which is why it is preferable in this temperature range to use continuously operating tube reactors with which it is possible to set a residence time of the reaction mixture as short as this. The reaction can be carried out at from 60° to 120° C., especially from 80° to 100° C., in systems either operating continuously or batchwise. The reaction time at below 60° C. is prolonged so that it is expedient to operate batchwise. Thus, for example, simply leaving the mixed reactant to stand in a container at room temperature results within a few days in the desired α-formylamino nitrile in a virtually quantitative yield based on cyanohydrin used. A procedure of this type can be particularly economic in, for example, smaller plants or for smaller batches.

The process according to the invention is generally carried out in such a way that the reactants are introduced into the reactor, mixed and heated to the intended temperature. The reaction is preferably carried out under the autogenous pressure of the system. Thus, stirred autoclaves are preferably used for batchwise operation, and pressure-stable tube reactors are preferably used, or particularly advantageously cascades of stirred vessels, for a continuous process. A solvent can also be added, if desired, to the liquid reaction mixture, but this is not usually necessary.

After the reaction is complete, work-up is generally by distillation, but it is also possible to isolate the desired product by extraction or crystallization. Where work-up is by distillation, the excess formamide and, where appropriate, the acid catalyst, especially when a carboxylic acid is used, and the α-formylamino nitrile I, if distillable, are removed from the ammonium salt which forms the bottom product. The product I is isolated for further use, while the acid catalyst, the formamide and the ammonium salt can be recycled to the reaction or used for other purposes, as required.

The present process can be used for preparing virtually any α-formylamino nitrile from the corresponding cyanohydrin. Thus, cyanohydrins II where $R^1$ and $R^2$ are each hydrogen or unsubstituted or substituted, with substituents which are inert under the reaction conditions, aliphatic or heteroaliphatic radicals with 1 to 10, cycloaliphatic or heterocycloaliphatic radicals with 3 to 6, araliphatic radicals with 7 to 12, heteroaraliphatic radicals with 4 to 12, aromatic radicals with 6 to 10 or heteroaromatic radicals with 3 to 10 carbon atoms, can be used in the process.

Heteroaliphatic radicals $R^1$ or $R^2$ can be alkoxy or polyalkoxy with up to 5 oxygen atoms. Moreover, aliphatic radicals $R^1$ and $R^2$ can be straight-chain, branched or connected together to form a 5- or 6-membered ring. Heterocycloalkyl, heteroaralkyl and heteroaryl radicals $R^1$ and $R^2$ can contain, in general, 1 or 2 of the hetero atoms nitrogen, oxygen and/or sulfur.

In order to indicate the range of applicability of the process according to the invention, examples of aldehydes and ketones whose cyanohydrins II can be used to produce α-formylamino nitriles advantageously by a process according to the invention are listed hereinafter:

formaldehyde, acetaldehyde, propionaldehyde, n-butyraldehyde, isobutyraldehyde, n-valeraldehyde, isovaleraldehyde, 2-methylbutylraldehyde, hexanal, benzaldehyde, phenylacetaldehyde, phenylpropionaldehyde, phenylisobutyraldehyde, 4-methylphenylacetaldehyde, 4-methoxyphenylacetaldehyde, 4-chlorophenylacetaldehyde, 2,6-dichlorobenzaldehyde, 4-hydroxyphenylacetaldehyde, 4-chlorobenzaldehyde, cyclopropanecarbaldehyde, cyclohexanecarbaldehyde, 1-methylcyclopropanecarbaldehyde, 2-pyrrolidone-3-propionaldehyde, tetrahydropyran-3-carbaldehyde, 1,4-dioxane-2-carbaldehyde, tetrahydrothiopyran-3-carbaldehyde, pyridine-2-carbaldehyde, pyridine-3-carbaldehyde, furan-3-carbaldehyde, furfurol, pyrrole-2-carbaldehyde, 4-imidazolyl-acetaldehyde, thiophene-3-carbaldehyde, 3-indolyl-acetaldehyde.

Furthermore, the process according to the invention can be used to prepare α-formylamino nitriles I whose heteroaliphatic radicals $R^1$ or $R^2$ preferably contain oxygen atoms as hetero atoms. The number of oxygen atoms in each heteroaliphatic radical can be up to 5, the number being, of course, dependent on the number of carbon atoms in the radical. The following groups are illustrative examples:

methoxy, ethoxy, propoxy, hexoxy, methoxyethylene, propoxyethylene-yl, methoxypropylene-yl, ethoxypropylene-yl, propoxypropylene-yl, oxyethylenemethoxy, oxyethyleneethoxy, oxyethylenepropoxy, oxyethylenehexoxy, bis(oxyethylene)methoxy, bis(oxyethylene)ethoxy, bis(oxyethylene)hexoxy, tetrakis(oxyethylene)methoxy, tetrakis(oxyethylene)ethoxy.

The cyanohydrins II can be prepared separately, stored and used for the reaction according to the invention as required. However, it is also possible to generate the cyanohydrins II immediately before the reaction according to the invention from the corresponding aldehydes, for example as described in U.S. Pat. No. 3,822,306, by reaction with hydrogen cyanide or salts thereof. Formamide is commercially available, as are the acids to be used as catalysts. The ammonium salts can be obtained, for example, by neutralization of aqueous solutions of the particular acids with ammonia, crystallization and drying.

The amount of gas produced in the process according to the invention is surprisingly reduced to about 2 liters per liter of reaction mixture. It is an advantage that the gas produced in the process according to the invention contains no hydrogen cyanide and can therefore be disposed of without difficulty. Other advantages of the process according to the invention are that small amounts of acidic catalyst are required, and the excess of formamide needed for complete reaction can be reduced to less than 2 mole of formamide per mole of cyanohydrin II. A particularly noteworthy point is the considerable improvement in the yield of α-formylamino nitrile I which can be achieved with the process according to the invention. For example, the yield of the nitrile of N-formylalanine increases from 82 to 95% of theory based on acetaldehyde cyanohydrin and from 75 to 94% of theory based on formamide. The nitrile of N-formylglycine, which has not hitherto been obtainable by the process of U.S. Pat. No. 3,822,306, is obtained in a yield of almost 90% according to the invention.

The α-formylamino nitriles obtainable according to the invention can be hydrolyzed as described in U.S. Pat. No. 3,822,306 to the corresponding amino acids. In addition, the α-formylamino nitriles obtainable according to the invention can be converted by thermal elimination of hydrogen cyanide by the processes of DE-A 16 68 038 and EP-B 184 074 into the corresponding formylamino alkenes which are used as monomers. For example, the nitrile of N-formylalanine obtainable according to the invention can be pyrolyzed by this process to give N-vinylformamide which is converted by the processes of EP-B 71 050 and EP-A into basic polymers which are used, for example, as auxiliaries in paper finishing.

EXAMPLE 1

A mixture of 71 g (1 mol) of acetaldehyde cyanohydrin (called lactonitrile hereinafter), 67.5 g (1.5 mol) of formamide, 6.4 g (0.14 mol) of formic acid and 16.4 g (0.26 mol) of ammonium formate was heated at 90° C. for 6 hours while stirring. During this 220 ml of gas containing carbon monoxide and carbon dioxide escapes. The resulting product mixture contains 92.8 g of nitrile of N-formylalanine, 6.2 g of formic acid, 22.1 g of formamide, 18.9 g of ammonium formate and 16.4 g of water and was fractionally distilled under reduced pressure. The yield of nitrile of N-formylalanine (boiling point 137° C./2 mbar) was 94.7 % based on lactonitrile and 93.8% based on reacted formamide.

EXAMPLE 2

The reaction was carried out as in Example 1 but with the addition of 8.2 g (0.13 mol) of ammonium formate as cocatalyst. The time until reaction was complete at 90° C. was 11 hours.

Yield of nitrile of N-formylalanine (based on lactonitrile): 94.3%.

COMPARATIVE EXAMPLE

The reaction was carried out as in Example 1 but without adding any ammonium formate. The time until reaction was complete at 90° C. was 18 hours.

Yield of nitrile of N-formylalanine (based on lactonitrile): 87.2%.

Yield of nitrile of N-formylalanine (based on formamide): 75%.

EXAMPLE 3

The reaction was carried out as in Example 1 but with the addition of 9.0 g (0.15 mol) of acetic acid in place of formic acid, and of 20.0 g (0.26 mol) of ammonium acetate in place of ammonium formate. Conversion after reaction at 90° C. for 5 hours was 98.3%. The resulting product mixture was worked up as in Example 1. Yield of nitrile of N-formylalanine (based on lactonitrile): 91.8%.

EXAMPLE 4

The reaction was carried out as in Example 1 but with the addition of 32.8 g (0.52 mol) of ammonium formate as cocatalyst. Reaction was complete after 3 hours at 90° C. Yield of nitrile of N-formylalanine (based on lactonitrile): 95.7%.

EXAMPLE 5

A mixture of 22.8 g (0.4 mol) of formaldehyde cyanohydrin, 36.1 g (0.8 mol) of formamide, 2.8 g (0.06 mol) of formic acid and 6.4 g (0.1 mol) of ammonium formate was heated at 90° C. for 12 hours. The resulting product mixture was then fractionally distilled under reduced pressure.

Yield of nitrile of N-formylglycine (boiling point 126° C./1 mbar): 89.7% (based on formaldehyde cyanohydrin).

EXAMPLE 6

A mixture of 48 g (0.425 mol) of isovaleraldehyde cyanohydrin, 38.3 g (0.85 mol) of formamide, 2.90 g (0.06 mol) of formic acid and 6.8 g (0.11 mol) of ammonium formate was heated at 90° C. for 5 hours. The resulting product mixture was then fractionally distilled under reduced pressure.

Yield of nitrile of N-formylleucine (based on cyanohydrin): 89%.

EXAMPLE 6

A mixture of 50.5 g (0.5 mol) of α-methoxyacetaldehyhde cyanohydrin, 45 g (1 mol) of formamide, 3.5 g (0.076 mol) of formic acid and 8.0 g (0.13 mol) of ammonium formate was heated at 90° C. for 8 hours. The resulting product mixture was then fractionally distilled under reduced pressure.

Yield of nitrile of N-formyl-β-methoxyalanine (based on cyanohydrin): 84%.

We claim:

1. A process for preparing an α-formylamino nitrile of the formula I

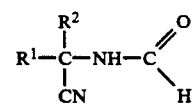

where $R^1$ and $R^2$ are each hydrogen or unsubstituted or substituted, with substituents which are inert under the reaction conditions, aliphatic or heteroaliphatic radicals with 1 to 10, cycloaliphatic or heterocycloaliphatic radicals with 3 to 6, araliphatic radicals with 7 to 12, heteroaraliphatic radicals with 4 to 12, aromatic radicals with 6 to 10 or heteroaromatic radicals with 3 to 10 carbon atoms, by reacting a cyanohydrin of the formula II

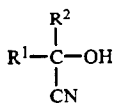

with formamide III

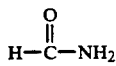

in the presence of acids, which comprises adding at least one ammonium salt to the reaction mixture.

2. A process as claimed in claim 1, wherein $R^1$ and $R^2$ in the cyanohydrin II are each hydrogen or $C_1$-$C_{10}$-alkyl, $C_3$-$C_6$-cycloalkyl, $C_7$-$C_{11}$-aralkyl or $C_4$-$C_{11}$-heteroaralkyl, $C_6$-$C_{10}$-aryl, $C_3$-$C_{10}$-heteroaryl, or $C_1$-$C_{10}$-heteroalkyl with 1 to 5 oxygen atoms.

3. A process as claimed in claim 1, wherein $R^1$ and $R^2$ in the cyanohydrin II are each hydrogen or $C_1$-$C_{10}$-alkyl.

4. A process as claimed in claim 1, wherein the reaction is carried out at from 20° to 150° C.

5. A process as claimed in claim 1, wherein the reaction is carried out at from 20° to 100° C.

6. A process as claimed in claim 1, wherein the ammonium salt is the salt of that acid used to catalyze the reaction.

7. A process as claimed in claim 1, wherein from 0.05 to 0.5 mole of ammonium formate is added per mole of cyanohydrin II in the reaction mixture.

8. A process as claimed in claim 1, wherein the reaction is carried out under the autogenous pressure of the system.

* * * * *